(12) United States Patent
Hopple et al.

(10) Patent No.: US 6,662,088 B1
(45) Date of Patent: Dec. 9, 2003

(54) METHODS AND SYSTEMS FOR INSPECTING AIRCRAFT FUSELAGE FRAMES

(75) Inventors: Michael Robert Hopple, Schenectady, NY (US); Elizabeth Lokenberg Dixon, Delanson, NY (US); Kenneth Gordan Herd, Schenectady, NY (US); Gregory Alan Mohr, Scotia, NY (US); Clifford Bueno, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/064,291

(22) Filed: Jun. 28, 2002

(51) Int. Cl.$^7$ .............................................. G06F 19/00
(52) U.S. Cl. ........................... 701/29; 701/301; 356/34; 73/767; 244/134 C; 901/10; 901/44; 901/46
(58) Field of Search .................. 701/29, 301; 356/33.5, 356/32, 33, 34; 73/767, 763, 760; 244/134 C, 134 R, 134 B; 901/9, 10, 20, 43, 44, 47, 50, 46; 324/242, 202

(56) References Cited

U.S. PATENT DOCUMENTS

| | | | |
|---|---|---|---|
| 3,940,952 A | 3/1976 | Mitchell .................. 73/67.8 R |
| 4,213,183 A | 7/1980 | Barron et al. ................ 364/507 |
| 4,237,454 A | 12/1980 | Meyer ......................... 340/682 |
| 4,480,480 A | * 11/1984 | Scott et al. .................... 73/769 |
| 4,583,854 A | 4/1986 | Lozar ......................... 356/237 |
| 4,647,220 A | * 3/1987 | Adams et al. ................. 374/5 |
| 4,813,062 A | 3/1989 | Gilpatrick .................... 378/162 |
| 4,873,708 A | 10/1989 | Cusano et al. ................. 378/62 |
| 4,943,732 A | 7/1990 | Economou ................... 250/572 |
| 5,111,048 A | 5/1992 | Devitt et al. ................. 250/342 |
| 5,112,566 A | 5/1992 | Butzin et al. ................ 376/245 |
| 5,197,361 A | 3/1993 | Carrier et al. ................ 82/1.2 |
| 5,399,968 A | 3/1995 | Sheppard et al. ........... 324/242 |
| 5,410,406 A | * 4/1995 | Webster ....................... 356/458 |
| 5,490,646 A | * 2/1996 | Shaw et al. ............. 244/134 C |
| 5,521,387 A | 5/1996 | Riedner et al. .............. 250/367 |
| 5,659,248 A | 8/1997 | Hedengren et al. ......... 324/242 |
| 5,805,664 A | 9/1998 | Whipple, III et al. ...... 378/117 |
| 5,836,068 A | * 11/1998 | Bullen et al. .................. 29/430 |
| 5,969,260 A | 10/1999 | Belk et al. ..................... 73/773 |
| 6,115,451 A | 9/2000 | Boudry et al. ............. 378/98.2 |
| 6,175,658 B1 | 1/2001 | Kump et al. ................ 382/266 |
| 6,236,049 B1 | 5/2001 | Thomas et al. ........... 250/341.6 |
| 6,239,438 B1 | 5/2001 | Schubert ................ 250/363.03 |
| 6,252,393 B1 | 6/2001 | Hedengren ................... 324/202 |
| 6,341,153 B1 | 1/2002 | Rivera et al. .................. 378/4 |
| 6,378,387 B1 | 4/2002 | Froom ....................... 73/865.8 |
| 6,399,948 B1 | 6/2002 | Thomas et al. .......... 250/341.6 |

* cited by examiner

Primary Examiner—Thomas G. Black
Assistant Examiner—Ronnie Mancho
(74) Attorney, Agent, or Firm—Penny A. Clarke; Patrick K. Patnode

(57) ABSTRACT

A method for inspecting an aircraft fuselage using an inspection system including a movable detector, wherein the method includes coupling a collision avoidance system to the inspection system detector, monitoring the collision avoidance system during operation of the inspection system, and controlling operation of the inspection system with the collision avoidance system.

15 Claims, 1 Drawing Sheet

METHODS AND SYSTEMS FOR INSPECTING AIRCRAFT FUSELAGE FRAMES

BACKGROUND OF INVENTION

This invention relates generally to aircraft fuselage frames, and more particularly to methods and systems for non-destructive inspection of aircraft fuselage frames.

In order to facilitate performing high-speed digital radiography for defect detection on passenger aircraft fuselage frames in both a timely and cost efficient manner, speed of data collection is primary. Speed can be addressed by rapid image acquisition, which can be accomplished through the synchronous motion of the energy source and the detector. In order to achieve adequate image quality, the detector must be located close to and along the outside of the aircraft fuselage to reduce the effects of magnification.

The proximity of the inspection system to the aircraft fuselage increases the potential for collision and damage to both the aircraft and the inspection system. To facilitate preventing collision and damage, at least some method of avoidance and protection is required.

SUMMARY OF INVENTION

In one aspect, a method for inspecting an aircraft fuselage using an inspection system that includes a movable detector is provided. The method includes coupling a collision avoidance system to the inspection system detector, monitoring the collision avoidance system during operation of the inspection system, and controlling operation of the inspection system with the collision avoidance system.

In another aspect, an apparatus for inspecting an aircraft fuselage is provided. The apparatus includes a movable detector, and a collision avoidance system in electrical communication with the movable detector to control the movable detector for inspecting the aircraft fuselage.

In another aspect, an inspection system for inspecting an aircraft fuselage is provided. The system includes a movable detector, at least one proximity sensor electrically coupled to the movable detector, and a collision avoidance system in electrical communication with the movable detector and the at least one proximity sensor for controlling the movable detector during the inspection of the aircraft fuselage.

DETAILED DESCRIPTION

Figure 1:
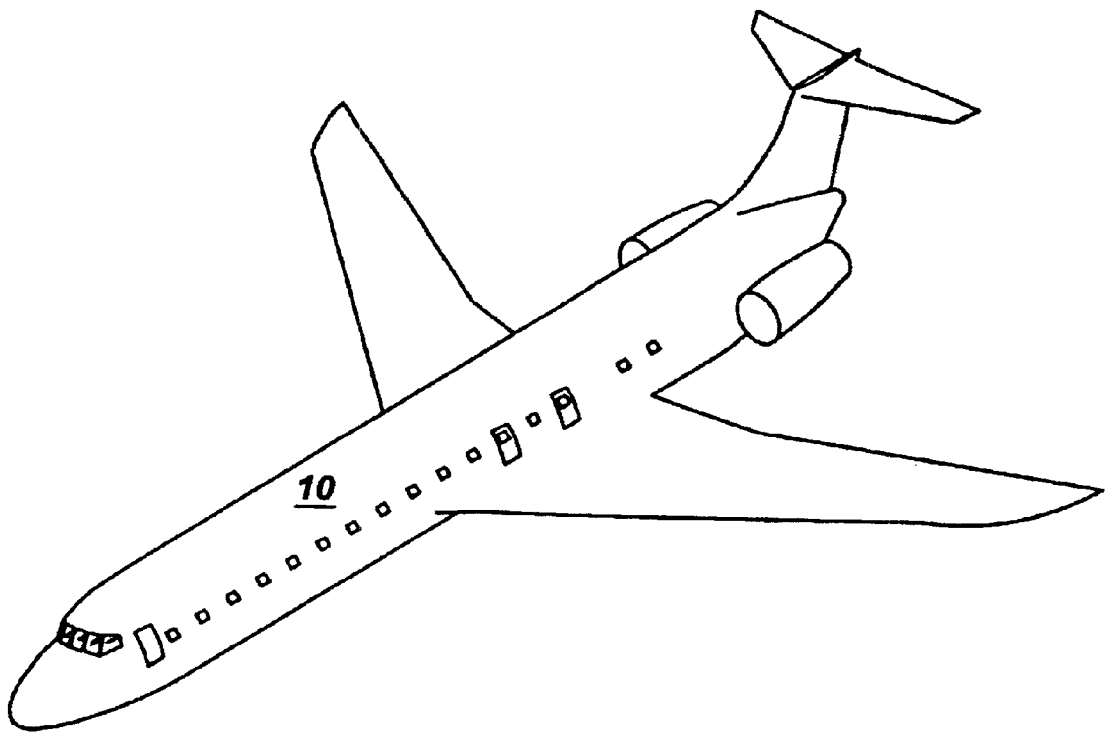
FIG. 1 is an illustration of an aircraft fuselage.
Figure 2:
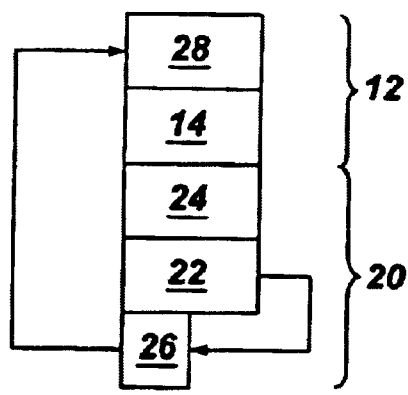
FIG. 2 is a block diagram of a collision avoidance system coupled to an inspection system for use with an aircraft fuselage.

FIG. 1 is an illustration of an aircraft fuselage 10 of a passenger jet. FIG. 2 is block diagram of an inspection system 12 for use with an aircraft fuselage, such as, aircraft fuselage 10 in FIG. 1. Inspection system 12 can detect defects in the aircraft fuselage, such as cracks, corrosion, delaminations, disbonds, etc. Inspection system 12 may also be used with other types of aircraft fuselages, structural components, and materials that include these types of defects. More specifically, inspection system 12 includes a movable detector 14 coupled in synchronous motion with an energy source (not shown). In one embodiment, inspection system 12 is a high-speed digital radiography system, such as the DXR-500 available from General Electric Inspection Technology, Cincinnati, Ohio. However, as will be appreciated by those in the art, other systems can be used within the scope of the present invention.

In operation, inspection system 12 rapidly passes close to and along fuselage 10. A collision avoidance system (CAS) 20 is coupled to inspection system 12 in order to prevent contact between inspection system 12 and fuselage 10 during the inspection process. CAS 20 includes at least one proximity sensor 22, at least one protection device 24, and a collision monitor 26. Proximity sensor 22 is electrically coupled to detector 14. In one embodiment, proximity sensor 22 is remotely coupled to detector 14. In one embodiment, proximity sensor 22 is a single sensor that includes at least an infrared sensor, an air-filled bladder sensor, or an accelerometer. In another embodiment, proximity sensor 22 is a group of sensors that includes a combination of at least an infrared sensor, an air-filled bladder sensor, or an accelerometer. An infrared sensor allows for measuring distance between detector 14 and fuselage 10. An air-filled bladder allows for monitoring changes in pressure and provides damage prevention. An accelerometer allows for measuring detector speed In operation, proximity sensor 22 generates signals during the operation of detector 14 and transmits those signals to collision monitor 26. If during the inspection process proximity sensor 22 detects an imminent collision, then a signal is transmitted to collision monitor 26. Monitor 26 is configured to send an imminent collision signal to an inspection system stopping mechanism 28. Stopping mechanism 28 is configured to immediately halt the motion of detector 14 and facilitate preventing a collision between detector 14 and fuselage 10. In one embodiment, stopping mechanism 28 is a manipulator that moves detector 14 away from fuselage 10.

A protection device 24 is coupled to inspection system 12. In one embodiment, protection device 24 includes, but is not limited to, one or a combination of at least an air-filled bladder, a balloon, or an airbag system. In another embodiment, protection device 24 includes other devices capable of protecting detector 14 as described herein.

Protection device 24 is in electrical communication with stopping mechanism 28 such that during operation, when stopping mechanism 28 receives an imminent collision signal from monitor 26, protection device 24 is deployed. Accordingly, detector 14 does not contact fuselage 10. In an alternative embodiment, protection device 24 is in electrical communication with proximity sensor 22 such that when proximity sensor 22 detects an imminent collision, protection device 24 is deployed and prevents contact between detector 14 and fuselage 10.

The above-described collision avoidance system 22 for an aircraft fuselage inspection system 12 is both cost-effective and highly reliable. The inspection system receives input from at least one proximity sensor coupled to the collision avoidance system to facilitate the prevention of contact between the movable detector and the aircraft fuselage. Furthermore, the collision avoidance system allows non-destructive inspections of aircraft fuselage frames. As a result, the inspection system can perform high-speed digital radiography on aircraft fuselages in close proximity without concern of damage to the detector or the fuselage or loss of image quality.

While the invention has been described in terms of various specific embodiments, those skilled in the art will recognize that the invention can be practiced with modification within the spirit and scope of the claims.

What is claimed is:

1. A method for inspecting an aircraft fuselage comprising:
   moving a detector along the aircraft fuselage;
   operating the detector to inspect the aircraft fuselage;
   coupling a collision avoidance system to the detector, the collision avoidance system comprising at least one proximity sensor, wherein said coupling comprises coupling the proximity sensor to the detector such that the collision avoidance system receives a plurality of signals from the proximity sensor during said operation of the detector;
   monitoring the collision avoidance system during said operation of the detector;
   generating an imminent collision signal in response to the signals from the proximity sensor; and
   controlling said movement of the detector with the collision avoidance system, including moving the detector away from the fuselage in response to the imminent collision signal.

2. A method for inspecting an aircraft comprising:
   moving a detector along the aircraft;
   operating the detector to inspect the aircraft;
   coupling a collision avoidance system to the detector, the collision avoidance system comprising at least one protection device, wherein said coupling comprises coupling the protection device to the detector to prevent contact between the detector and the aircraft, and wherein the protection device comprises at least one of an air-filled bladder sensor, a balloon, and an airbag system;
   monitoring the collision avoidance system during said operation of the detector; and
   controlling said movement of the detector with the collision avoidance system.

3. A method in accordance with claim 2, wherein the collision avoidance system further comprises a proximity sensor, wherein said method further comprises generating an imminent collision signal in response to a signal from the proximity sensor, wherein said controlling step includes deploying the protection device in response to the imminent collision signal.

4. An apparatus for inspecting an aircraft fuselage comprising:
   a movable detector;
   a collision avoidance system in electrical communication with said movable detector to control movement of said movable detector; and
   at least one proximity sensor coupled to said movable detector,
   wherein said proximity sensor is coupled to said collision avoidance system such that said collision avoidance system receives a signal from said proximity sensor during operation of said moveable detector,
   wherein said proximity sensor generates an imminent collision signal and transmits the signal to said collision avoidance system, and
   wherein said collision avoidance system controls the movement of said moveable detector based on the signal received from said proximity sensor, including moving said movable detector away from the aircraft fuselage in response to the imminent collision signal.

5. An apparatus in accordance with claim 4, wherein said at least one proximity sensor comprises at least one of an infrared sensor, an air-filled bladder sensor, and an accelerometer.

6. An apparatus in accordance with claim 4, wherein said collision avoidance system further comprises a stopping mechanism coupled to said moveable detector and configured to receive the imminent collision signal and to stop the motion of said moveable detector.

7. A method in accordance with claim 6, wherein said stopping mechanism comprises a manipulator for moving said movable detector away from the aircraft fuselage in response to the imminent collision signal.

8. An apparatus in accordance with claim 4, wherein said moveable detector comprises a digital x-ray detector.

9. An apparatus for inspecting an aircraft fuselage comprising:
   a moveable detector;
   a collision avoidance system for controlling movement of said moveable detector, said collision avoidance system comprising at least one protection device for preventing contact between said moveable detector and the aircraft fuselage, wherein said protection device comprises at least one of an air-filled bladder, a balloon, and an airbag system.

10. An inspection system for inspecting an aircraft comprising:
    a moveable detector;
    at least one proximity sensor coupled to said moveable detector; and
    a collision avoidance system coupled to said moveable detector and said at least one proximity sensor for controlling said moveable detector during the inspection of the aircraft in response to a signal from said proximity sensor,
    wherein said proximity sensor generates an imminent collision signal and transmits the signal to said collision avoidance system, and wherein said collision avoidance system moves said movable detector away from the aircraft in response to the imminent collision signal.

11. A system in accordance with claim 10, wherein said at least one proximity sensor comprises at least one of an infrared sensor, an air-filled bladder sensor, and an accelerometer.

12. A system in accordance with claim 10, wherein said collision avoidance system further comprises at least one protection device for preventing contact between said moveable detector and the aircraft in response to the imminent collision signal.

13. A system in accordance with claim 12 wherein said at least one protection device comprises at least one of an air-filled bladder, a balloon, and an airbag system.

14. A system in accordance with claim 10, wherein said moveable detector comprises a digital x-ray detector.

15. A system in accordance with claim 10, wherein said collision avoidance system comprises:
    a monitor for receiving the signal from said proximity sensor, wherein said monitor is configured to generate the imminent collision signal; and
    a manipulator for moving said movable detector away from the aircraft in response to the imminent collision signal.

* * * * *